(12) United States Patent
Fraser

(10) Patent No.: US 9,222,926 B1
(45) Date of Patent: Dec. 29, 2015

(54) METHODS AND ARTICLES FOR IDENTIFYING OBJECTS USING ENCAPSULATED PERFLUOROCARBON TRACERS

(71) Applicant: Tracer Detection Technology Corp., San Antonio, TX (US)

(72) Inventor: Jay Fraser, San Antonio, TX (US)

(73) Assignee: Copilot Ventures Fund II LLC, Wilmington, DE (US)

( * ) Notice: Subject to any disclaimer, the term of this patent is extended or adjusted under 35 U.S.C. 154(b) by 295 days.

(21) Appl. No.: 13/955,460

(22) Filed: Jul. 31, 2013

Related U.S. Application Data

(63) Continuation of application No. 13/442,847, filed on Apr. 9, 2012, now Pat. No. 8,501,481, which is a continuation of application No. 12/702,236, filed on Feb. 8, 2010, now Pat. No. 8,153,435, which is a continuation of application No. 11/393,556, filed on Mar. 30, 2006, now abandoned.

(60) Provisional application No. 60/666,477, filed on Mar. 30, 2005.

(51) Int. Cl.
*G01N 37/00* (2006.01)
*G01N 33/00* (2006.01)

(52) U.S. Cl.
CPC .................................. *G01N 33/0004* (2013.01)

(58) Field of Classification Search
None
See application file for complete search history.

*Primary Examiner* — Dirk Bass
(74) *Attorney, Agent, or Firm* — Steven M. Hoffberg, Esq.; Ostrolenk Faber LLP

(57) ABSTRACT

A system and method for tagging, tracking, locating and identifying people and vehicles transporting people using Perfluorocarbon tracers. An on-going problem faced by military as well as law enforcement personnel is that of friendly fire incidents. To prevent possible friendly-fire incidents, troops would separate the two layers of the uniform patch, thereby releasing a controlled release of the Perfluorocarbon vapors. Other "friendly" troops, equipped with sensors tuned to the specific perfluorocarbon characteristics would thus be able to literally view a plume around the tagged person or object. The system may conversely be used to tag enemies. Formulations of mixed perfluorocarbons may be used to provide coding of emissions.

20 Claims, 1 Drawing Sheet

*Taggant Capsules on Substrate with Barrier Layer*

*Ruptured Capsules*

*Taggant Capsules on Substrate with Barrier Layer*

*Ruptured Capsules*

METHODS AND ARTICLES FOR IDENTIFYING OBJECTS USING ENCAPSULATED PERFLUOROCARBON TRACERS

RELATED APPLICATIONS

The present application is a Continuation of U.S. patent application Ser. No. 13/442,847, filed Apr. 9, 2012, now U.S. Pat. No. 8,501,481, issued Aug. 6, 2013, which is a continuation of U.S. Ser. No. 12/702,236, filed Feb. 8, 2010, now U.S. Pat. No. 8,153,435, issued Mar. 21, 2012, which is a continuation of U.S. patent application Ser. No. 11/393,556, filed Mar. 30, 2006, abandoned, which claims benefit of priority from U.S. Provisional Patent Application Ser. No. 60/666,477, filed Mar. 30, 2005, each of the entirety of which are expressly incorporated herein by reference.

BACKGROUND OF THE INVENTION

Perfluorocarbons are generally non-toxic, safe, volatile, non-reactive, compounds, which are environmentally benign, especially when released on limited quantities. The ambient background concentrations of the five perfluorocarbons routinely used as tracers (PFTs) are in the range of parts per $10^{15}$ of air. The PFTs, by virtue of their high vapor pressure, provide the unique ability to permeate closed doors and windows, containers and luggage. On the other hand, PFTs can be optically or physically detected, and are impervious to electronic interference and other problems inherent with other tagging technologies. Once a location reaches steady state, the actively emitting tagged item will provide vapor traces that are detectable in the vicinity of the item (even temporarily following removal of the tagged item). By extending the detectable life of the perfluorocarbon tag materials, PFTs have been previously known to provide a unique tool for law enforcement in numerous applications including marking and tracking of currency and other non-invasive inspection scenarios when seeking various items of contraband under surveillance.

PFT technology has already been developed and utilized in various applications including: (1) detection of leaks in underground storage tanks; (2) detection of leaks in high-pressure, oil-filled electric transmission lines; (3) atmospheric tracing and air pollution dispersion studies; (4) building ventilation studies; (5) detection of tagged explosives (blasting caps) in airline luggage; (6) detection of leaks in natural gas pipelines; and (7) currency tracking in cases of kidnappings. It has also been proposed for early warning fire detection systems.

U.S. Pat. Nos. 3,991,680 and 4,256,038, expressly incorporated herein by reference, relate to methods of detecting small bombs to provide security against terrorist activities which can cause the destruction of civil aircraft in flight or detonate explosives in places where large groups of people congregate. These methods involve the tagging of explosive materials such as blasting caps with a so-called "vapor taggant" which can be "sniffed" and detected by suitable equipment. The vapor taggant disclosed in U.S. Pat. No. 3,991,680 is sulfur hexafluoride (SF.sub.6) absorbed in a fluoro-polymer. The vapor taggant disclosed in U.S. Pat. No. 4,256,038 is includes one or a plurality of the following compositions: perfluorocycloalkanes such as perfluorodimethylcyclobutane (PDCB), perfuoromethylcyclohexane (PMCH), and perfluorodimethylcyclohexane (PDCH); perfluoroaromatics such as hexafluorobenzene (HFB), octafluorotoluene (OFT), decafluorobiphenyl (DFBP), decafluoroxylene (DFX), octafluoronaphthalene (OFN), and pentafluoropyridene (PFP), perfluoroalkanes such as perfluorohexane (PFH), perfluoropentane (PFPT), and perfluorooctane (PFO), and perefluorocycloalkenes such as decafluorocyclohexene (DFCH) and octafluorocyclopentene (OFCP). Examples of elastomers which are compatible with several of these taggants are copolymers of vinylidene fluoride and hexafluoropropylene. The following PFT compositions are also particularly useful as taggants: pf-methylcyclopentane (PMCP); pf-1,2-dimethylcyclohexane (o-PDCH[1]); pf-1,3-dimethylcyclohexane (m-PDCH[1]); pf-1,4-dimethylcyclohexane (p-PDCH[1]), pf-trimethylcyclohexanes (PTCH), perfluorodecalin (Octadecafluorodecahydonaphthalene, PFD, CAS 306-94-5), and perfluoro(methyl)decalin (PFMD, CAS 306-92-3). These compositions may be combined, as desired, to form a specific "cocktail"; i.e., a taggant that can be selectively detected and discriminated with respect to other taggants.

As used herein. PFT's are intended to refer to a class of chemical entities which have at least one —$CF_2$—$CF_2$— portion, or otherwise has an optical spectral characteristics corresponding to those resulting from the highly electronegative fluorine substituents, such that the compound is spectrographically distinguishable at very low concentrations, i.e., less than ppm level, and preferably less than ppb levels, from environmentally common substances. In some cases, a non-perfluorinated fluorocarbons may also be suitable for use, and to the extent that these have similar or advantageous remote detection characteristics, have low toxicity, good environmental stability (but perhaps less so than the perfluorocarbons, to reduce detrimental long-term environmental persistence and global warming potential), and appropriate volatility and dispersion in air, these may also be included with the scope of PFTs as encompassed herein.

Taggant use involves the detection of gaseous vapors (in minor tracer quantities) that are emitted over time. As there are a plurality of separate usable tracers in the PFT family, each with its own "fingerprint", the PFTs can be combined in a range of combinations and concentrations, yielding thousands of discrete "signatures". This allows discrimination between various compositions and enables the individual detection of multiple products, or the tracking of individually tagged products to provide exact identification and location.

The PFT technology is the most sensitive of all tracer technologies because the ambient background levels of the routinely used PFTs are extremely low (in the range of parts per quadrillion-ppq), and PFTs can be measured down to those levels.

It is the physical and chemical inertness of the PFTs that not only prevents their loss in the atmosphere, but also helps in their separation and analysis from less stable interfering compounds and makes them biologically inactive; and thus safe to use. Their limited industrial use not only results in low ambient background concentration, but also limits the possibility of numerous higher local concentrations that might confuse detection capability.

John H. Heiser and Arthur J. Sedlacek, "Using LIDAR to Measure Perfluorocarbon Tracers for the Verification and Monitoring of Cap and Cover Systems", Brookhaven National Laboratory (2005), www.ecd.bnl.gov/pubs/BNL-75583-2006-JA.pdf, expressly incorporated herein by reference, teaches the use of LIDAR to detect PMCH, a perfluorocarbon.

Mason K Harrup, "Use of Custom Polyphosphazenes as Tunable Matrices for the Controlled Release of PFTs" (White Paper), expressly incorporated herein by reference, discloses a "tuned" polyphosphazene matrix, having a balance of perfluoronated pendant groups designed to hold the PFT tightly, providing slow release, and polar pendant groups designed to be incompatible with the PFT, providing fast release, to thereby control the observed PFT release rate.

U.S. Pat. No. 6,025,200, expressly incorporated herein by reference, relates to remote optical detection of PFTs. According to U.S. Pat. No. 6,025,200, cyclodextrins, liposomes, and synthetic polymer systems can be used in the development of encapsulated PFTs. As a group, these technologies provide a menu of tracer devices which can be tailored to meet a specific need. Cyclodextrin-PFT complexes can be formulated as a dispersion, true solution, or as solid crystalline powder. The cyclodextrin-PFT complexes can be made in water or mixed solvent systems and isolated as a free-flowing powder by spray drying or filtration from the mother liquor. The complex can be formulated in its mother liquor or used as a true solution or dispersion.

U.S. Pat. No. 6,214,624, expressly incorporated herein by reference discloses the use of PFTs to track hydrocarbon liquids. U.S. Pat. No. 5,409,839, expressly incorporated herein by reference, is entitled and describes a method for the tagging and detection of drugs, crops, chemical compounds and currency with perfluorocarbon tracers. U.S. Pat. No. 6,617,591, expressly incorporated herein by reference, relates to remote detection of explosives, for example, buried mines. See also, U.S. Pat. Nos. 4,520,109, 5,173,298, 5,362,568, 5,585,112, 5,853,752, 6,071,495, and 6,196,056, expressly incorporated herein by reference.

DESCRIPTION OF THE INVENTION

Figure 1A:
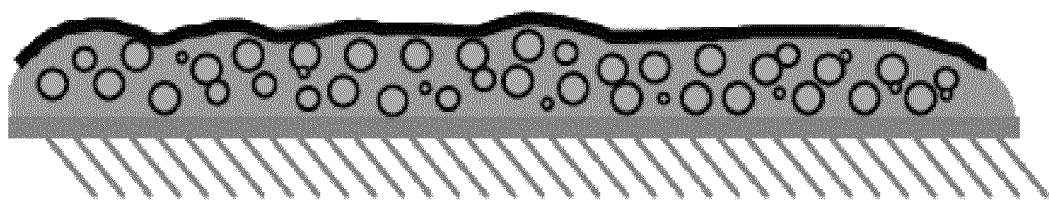
FIGS. 1A and 1B show representative cross sections of a tracer releasing apparatus having taggant capsules within a matrix, on a barrier layer, before and after release of the barrier.

According to one embodiment of the invention, a method is provided for using Perfluorocarbon Tracers to Identify Personnel (Friend or Foe) on the Battlefield, e.g., traditional or urban. For example, an encapsulation formula of Perfluorocarbon tracers can be impregnated into one or both of the layers of separable patch, which prior to separation, has a minimal rate of PFT release, and after separation, has a steady rate of release sufficient to allow remote detection. The patch, for example, may be a tear-away Velcro patch adapted to be affixed to soldiers in a war zone. To prevent possible friendly-fire incidents, troops would separate the layers of the patch, thereby initiating a controlled release of the PFT vapors. Other "friendly" troops on the field of battle, equipped with sensors for the PFT emissions, which may operate passively by detecting absorption or fluorescent emission from normal light sources, or actively by stimulating optical emissions and/or measuring specific absorption. At night, for example, illuminators tuned to the fluorescent wavelength of the Perfluorocarbon gases and specially designed, wavelength-matched vision devices would thus be able to literally "visible" as a cloud that might surround or emanate directly from the friendly troops. Likewise, an automated system could be provided to automatically block fire against friendly troops, bypassing the user's discretion, and perhaps acting with faster response and accuracy.

Alternately, a tag may be placed on personnel or objects, to assist in tracking them. For example, a patch, liquid, or powder, may be surreptitiously applied to an enemy vehicle, which could then be tracked to its destination. In this case, the tag may also be used to guide munitions, rather than inhibit them.

In a normal scenario, multiple taggant compositions and combinations may be employed, for various purposes. Thus, even if an enemy were to gain control over a set of tags, it would have to know the encoding, which could change periodically, in order to effectively use them as a false defense or offensive tool.

Likewise, the detector may be provided which requires authentication, such as biometric, token, security code, or the like, which would impede unauthorized use. This technique is especially useful where the PFTs themselves are dynamically encoded, and therefore without certain secret knowledge, the output of the detector would be difficult to interpret at any given time. For example, according to one embodiment, the PFTs release a time coded coded plume, which may alternately indicate friend, foe, or other identification. Likewise, release of dummy PFTs may be employed, to obscure particularly encoded releases, and thus requiring a sophisticated detector.

It is noted that a sophisticated adversary might seek to develop measures to track a reading device, and thus a passive (relying on ambient illumination) or remotely operable illuminator is preferred in such circumstances. Likewise, it is preferred that the reader incorporate at least one sophisticated and difficult to obtain critical technology, to impede unauthorized recreation.

It is also useful to provide an interrogator detection system, in the event that unauthorized devices are or become available, so that the badge wearers can take immediate action to avoid personal or other risk, when an unauthorized interrogator is detected. For example, authorized interrogators may produce a cryptographically encoded emission, the authenticity of which is determinable by an authentication device. Even in the event that an authentic device is diverted, the encoding may be device-specific, permitting individual detection and countermeasures to be employed, without requiring all authorized devices to be modified. For example, if an interrogator includes a laser illuminator, the laser itself, or an associated signal, may be individually modulated corresponding to an encoded signal. In the event of an unencoded, unauthorized, or deauthorized encoding in an illuminator suitable for detecting PFTs, users can immediately detect this illuminator when targeted by it, and take countermeasures, such as targeting the illuminator for destruction, and removing the PFT emitting devices from their person or vehicles. The detectors may also be protected by code or biometrics, to prevent their unauthorized use.

It is noted that since there are a number of usable compounds which are perfluorocarbons, or are closely related to perfluorocarbons, a large number of "recipes" are available. Therefore, it is preferred that the reader or interrogator permit individual detection of the various usable compounds, as well as distinguishing the components of a mixture and/or quantitatively determine ratios thereof. Typically, this detection will employ a laser illuminator to determine a specific spectrographic and/or fluorescence optical response of each PFT employed.

The reader or interrogator will typically employ a narrow bandwidth directional illumination source. The specific absorption wavelengths for perfluorocarbons and related compounds are in the UV range. Thus, a suitable illuminator would be a filtered broadband lamp, UV LED, LED (or other source) excited photon capture UV fluorescent emitter, a laser, or other emission source. Typically, a high efficiency design is preferred, since a low efficiency illuminator would emit heat and have high power demands, limiting portability and duration of battery life. Thus, a preferred design employs an LED excited emitter, or electroluminescent design, to provide a significant battery life and a low level of undesired emissions.

The detector is typically a spectrophotometric-type detector, capable of distinguishing specific PFT signatures from interfering emissions or absorptions. It is also preferably battery operated and small. The detector may also be provided as a broadband sensitive detector with one or more specific filters.

The PFT emitting device itself is, for example, a flat sheet-like patch, for example 1-25 square inches, composed of two sheets which are impermeable to perfluorocarbon vapors. These may be, for example, metallized or aluminized Mylar® Biaxially-oriented polyethylene terephthalate (boPET) polyester film, or other suitable material. A base sheet preferably has a removable attachment means, such as Velcro®, snaps, magnets, or other suitable method for removable attachment, e.g., to a uniform or object. Between the sheets is a controlled release perfluorocarbon material. For example, a polyphosphazine matrix, wax, or other material impregnated with PFT's, or microencapsulated PFT's in a matrix, is provided, which selectively adheres to the base sheet. The controlled release perfluorocarbon material is covered during storage with a cover sheet which is removable, and which easily releases from the controlled release perfluorocarbon material. For example, an adhesive or heat-generated seal is formed around the periphery junction of the two sheets, which is frangible when subjected to a peeling force.

While a relatively homogeneous material (i.e., homogeneous matrix or embedded microcapsule matrix) is preferred, a macroscopic barrier or atomizer may also be used to control release of PFT. In the later case, a pump, MEMS device, piezoelectric device, bubble jet, or other electrically operated device may be operated to release PFT. Such a device could have an electronic control, capable of arbitrary release profile generation, and remote activation/deactivation. Likewise, the device could employ separate control over a plurality of tracers, each with a separate release profile. Thus, an authorized device could have a predefined but secret temporal release profile (for example defined by a cryptographic function), allowing authentication of PFT releasing devices. The device could further have RF-ID attributes and/or a wireless receiver for remote controllability. Advantageously, an electronic embodiment employs a zinc air battery, activated by unsealing, and thus storage stable and activated along with the release of PFTs. Indeed, a film battery technology may permit formation of the battery together with the film forming the barrier to contain the PFT prior to intended release. Typically, a seal is provided for storage, since even low levels of unintended leakage over time will deplete the device and potentially pollute the atmosphere, making specific detection more difficult.

During storage, the sheets thus prevent release of PFT, while when the cover sheet is removed, the PFT is continually or controllably released over an extended period. It is preferred also that, in a passive device, the release be at a relatively constant rate. Various known methods for temporally controlling release rates, such as employed in conjunction with pharmaceuticals, may also be employed. See, e.g., Temporal Control of Drug Delivery, Hrushesky, Langer, & Theeuwes, Eds., NY Acad. Sci 618 (1991), expressly incorporated herein by reference, and especially, Langer, Robert & Kost, Joseph, "Real Time Response Polymeric Delivery Systems", pp. 330-334.

Preferably, the PFT is not a single material, but at least two different materials, which are combined such that they are both released in detectable quantities. This combination permits coding of the patches, and makes counterfeiting more difficult. It likewise facilitates detection, since the composite spectral signature will have more features available for analysis. It is noted that, in the case of a combination release, it is possible to employ a different composition entirely, for example one that is not a PFT. Preferably, the detection system for the plural compositions will include substantial common elements, although this is not required.

Another aspect of the invention provides a method of using tracers to identify "friendly" vehicles, e.g., on the battlefield. For example, an encapsulated formulation, either in the form of a patch, or aerosolized by an aerosolizing apparatus, can used in conjunction with a vehicle, for example, tanks, HUMVEES, personnel carriers, Jeeps, etc. The vehicle will this emit a distinguishable plume, which can be remotely detected by its characteristic fluorescent pattern, can be used to identify various "friendly" vehicles. The detector can be used as part of a manual weapons targeting system, or as part of an automated trigger inhibition or fusing system.

On the other hand, such a plume may also be used to target or track vehicles (e.g., enemy or suspect) or other objects, especially where it is not the vehicle, but its future contents, which are of interest, since tagging the vehicle will generally require intimate contact.

A further aspect of the invention provides a method and composition for tracking, detecting and/or identifying suspected terrorists or criminals by ingestion, or for tracking potential kidnap or abduction risks. It has been determined that following exposure to perfluorocarbon materials that a human subject will emit a detectable chemical signal of perfluorocarbon for a period of up to one month, or longer depending upon individual metabolism and exposure dosage. The perfluorocarbons are emitted through bodily pores, excreted bodily fluids, and/or exhalation.

It is thus known that perfluorocarbons can be retained in the human body for extended periods of time. This is particularly obvious in the presence of technologies such as the DSITMS which provides very low detection levels in real-time. In the course of preparing for the demonstrations described below, it was noted that perfluorocarbon could be detected from one of the researchers at the Oak Ridge National Laboratory (breath, skin, urine) for three days after limited contact with a wax crayon formulation. Perfluorocarbons are nonmetabolizable, however, they do induce hepatic metabolizing enzymes. PFD given to rats was shown to induce cytochrome P-450 in a manner similar to phenobarbital. As with Phenobarbital induction, the activities of cytrochrome P-450 IIA1 and IIA2 (a.k.a. cytochrome P450b and cytochrome P450e) were increased approximately two-fold following PFD treatment. Likewise, the activities of benzphetamine-N-demethylase and aldrin-epoxidase were increased. The activities of cytochrome P-450 IA1 and IA1 (induced by 3-methylcholanthrene-type inducers) and cytochrome P450 IV (induced by fatty acids and perfluoronated fatty acids) were unaffected. Although the perfluorocarbons are sequestered in the fat and later transferred to the liver, over time they are eliminated from the body via the lungs by exhalation. See, Final Report for CRADA Number ORNL99-0562, under funding from Tracer Detection Technology Corp. under contract of the National Institute of Justice, Jul. 26, 2000.

By incorporating encapsulated Perfluorocarbon tracers into food stuffs or other supplies or provisions anticipated to be delivered to, being transported to the hideouts of, or ingested by mammals of interest, the location, even if hidden, can be remotely detected. In this embodiment, preferably a pure form of PFT, or an encapsulation formulation thereof, in which the PFT can be mixed with food, other ingestible items or other supplies which are ultimately ingested, will emit a plume of the vapor taggant that can be detected through various means of sensing. Alternately, the PFT is released or volatilized during cooking, and thus the location of a "hideout" may be determined by searching for an associated plume from this release. Therefore, the PFT may be absorbed in, or placed in conjunction with, a food which requires cooking, such as rice.

The present invention further encompasses a method of using PFTs to track, detect and identify suspected terrorists or criminals, or hideouts of terrorists or criminals, by marking vehicles suspected of traveling to terrorist or criminal hideouts or other objects which are carried to these locations.

Effective inspection of large containers and trucks for controlled substances and narcotics is essential for the success of drug interdiction efforts. A significant fraction of drugs are smuggled through this avenue. Without prior knowledge provided through intelligence activities, the chances for drug detection are very slim. A successful drug interdiction program therefore requires efficient, rapid and cost-effective inspection techniques for large objects. The current technique used to thoroughly inspect containers is manual, highly labor intensive and can hardly be expanded to meet the challenge of abating the flow of illicit drugs from one country to another. Hence, an efficient way to meet the goal of an effective counter-drug effort is to provide a rapid, automatic, non-intrusive inspection system to inspect shipments and cargo containers without removing all of the contents for manual inspection. Thus, if a shipment can be tagged near its point of origin, it may be tracked using PFTs to distribution, permitting an entire chain to be tracked, without seizing the contraband at an intermediate stage.

In order for PFT tagging to function effectively, the release should be of sufficient concentration as to enable unambiguous identification, and also should be sufficiently long-lasting as to fulfill various usage parameters. Thus, in order to provide a sustained release of PFTs, a matrix is provided which provides a desired release profile. One type of matrix is a paraffin wax matrix or one based on large molecule inclusion complexes, however, such matrices may be difficult to control.

Polyphosphazenes are a class of polymers with backbones consisting of alternating phosphorus and nitrogen atoms. A repeating unit in polyphosphazenes is shown below, where the side groups G can be organic, inorganic or organometallic, and need not be the same. Interest in these polymers relies on the fact that, compared to various other biodegradable polymer materials, polyphosphazenes are easier to manipulate with different side groups. In addition, their physical and chemical properties are greatly affected by the nature of the side groups. Therefore, polymers with a wide range of properties can be obtained by appropriately choosing side chain groups. The possibility of obtaining polyorganophosphazene with different tunable properties makes those polymers potentially useful in many fields, ranging from pharmaceutical, industrial to agricultural applications. See, Shan Cheng, Stimuli-Responsive Polyphosphazenes as Controlled Drug Delivery Matrix Materials (2001), dspace.library.drexel.edu/retrieve/963/end.pdf.

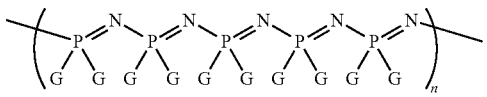

Two different fundamental routes to synthesize substituted polyphosphazenes are generally used. A first method one starts from substitution reactions of the chlorine atoms on hexachlorocyclotriphosphazene to prepare phosphazene cyclic trimers with different side groups.

By ring-opening polymerization of these small cyclic trimers, polyphosphazenes with different substituents can be obtained.

Many new materials have been prepared through this direct synthesis. However, the steric hindrance effect greatly limits the variety and the amount of the substituent on polymer chains. To solve this problem Allcock and his co-workers developed a synthesis route which involves the preparation of poly(dichlorophosphazene) and a sequential substitution reaction of chlorine atoms. In the first step, poly(dichlorophosphazene) as highly reactive macromolecular intermediate, can be prepared by several different methods. The most effective route to high molecular weight poly(dichlorophosphazene) is via the ring-opening polymerization of the cyclic trimer, hexachlorocyclotriphosphazene at 250° C. in the molten phase or in solution. This reaction gives a polymer with a broad molecular weight distribution, but with an Mw near 2,000,000, which corresponds to approximately 15,000 repeating units per chain. More recently, a room-temperature, living cationic condensation polymerization of Me3SiN=PC13 method has also been developed. This reaction yields narrow molecular weight distribution polymers, with excellent control of the molecular weight and access to block copolymers.

The second step in the synthesis involves the replacement of the chlorine atoms by reactions with different organic or organometallic groups. Typically, an average of 30,000 chlorine atoms per molecule could be replaced at this stage as the result of high reactivity of the P—Cl bond. Based on this macromolecular substitution reaction, several hundred different polyorganophosphazenes have been synthesized. Most of the current industrial important polyphosphazenes are made by this method.

As a relatively new biodegradable polymer, polyphosphazene as drug delivery material has been widely studied. Compared with other drug delivery matrix materials, polyphosphazene shows particular advantages because it has an inorganic backbone that is biocompatible over time and that degrades to harmless small molecule products: ammonia, phosphate, and water. The system can be tailored to respond to different physiological environmental conditions by appropriate choice of substituted side chains. Many results show that the delivery systems designed with this material can accommodate a large variety of drugs including small drugs and macromolecules.

Release study has been explored with both hydrophobic and hydrophilic polyphosphazene. The former ones are usually studied for polymer matrix erosion and diffusion release systems, while the latter ones are used to prepare hydrogel matrices after being crosslinked.

With respect to perfluorocarbons, it is well known that they have a high self-affinity, and this a fluorinated alkyl or perfluorinated substituent will be compatible with the PFT, thus leading to a high loading capacity and slowed release. Likewise, PFTs are incompatible with polar substituents, leading to lower loading capacity and higher release rates. As is known, the properties of a matrix may be tailored by balancing the proportions of the various substituents.

An alternate method for controlling release rate of PFTs is to provide a mechanical barrier, such as a perforated sheet, which allows volatilization dependent on the perforated area. In this case, the release rate is decoupled from the PFT holding capacity, though the mechanical structure is somewhat more complex and the composite structure will be more sensitive to mechanical treatment during use.

Figure 1B:
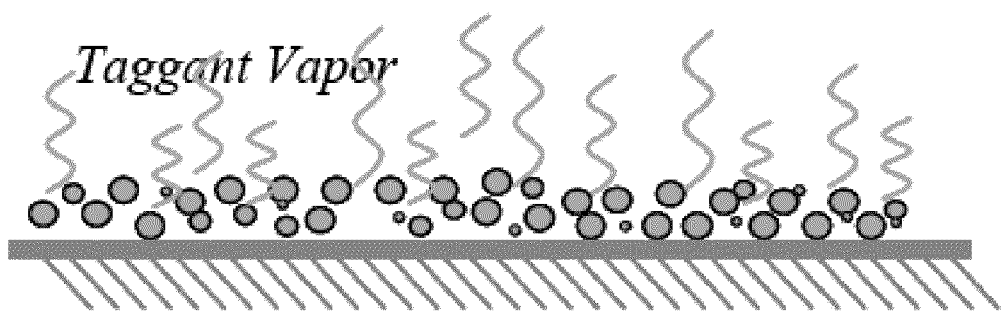

Indeed, both a matrix and a barrier technique may be combined, for example as shown in FIGS. 1A and 1B. FIG. 1 shows a representative cross section of a perfluorocarbon tracer having taggant microcapsules within a matrix, on a carrier layer, before and after release of a cover layer. The taggant capsules provide a relatively high bulk storage capacity, while the matrix provides release profile control. Typically, the matrix will be saturated with taggant, with the capsules providing a replenishing source. The release rate will be dependent on the surface area and an air-matrix release coefficient for the taggant, which in turn will be dependent on the vapor pressure of the taggant and the affinity of the matrix for the taggant.

The present invention therefore provides a system and method for identifying and tracking persons and objects, comprising use of a controlled taggant release device which has a very low rate of release prior to activation, and has an extended duration consistent rate of release after activation, which may be conveniently applied to persons or objects.

The present invention also provides a system for detection of taggant release device, comprising remote optical detection system which employs an illuminator emitting an optical wavelength for exciting a fluorescent emission from a taggant, and an imaging detector for sensing and/or imaging the excited fluorescence. This detector is preferably battery operated, portable by a human. The device may operate independently, but is preferably integrated with a fusing or triggering mechanism for munitions. The device is further preferably configured as part of an "identify friend or foe" (IFF) system, which may be manually or automatically operable. In one embodiment, the detector or imager is mounted on an unmanned vehicle, such as an unmanned aerial vehicle (UAV).

It is therefore an object of the invention to provide a method of using volatile perfluorocarbons to identify personnel, comprising the steps of applying a selectively activatable controlled release perfluorocarbon to a person. Preferably, the controlled release mechanism employs a substituted polyphosphazene matrix. The PFT is preferably one or more perfluorocarbons selected from the group of PMCH, PMCP, o-PDCH', m-PDCH', p-PDCH' and PTCH. The controlled release is preferably initiated by removal of a barrier, such as a confining film. Preferably, the controlled release continues after initiation for 4-48 hours, and thereafter occurs at only a low level. Longer duration formulations may also be provided. The PFT matrix may be provided as an aerosol, paint or powder. The PFT is preferably released from a substituted polyphosphazene matrix, formulated to control a capacity and release profile of the PFT from the matrix.

The volatile perfluorocarbons may also be used to identify land vehicles. Thus, according to another embodiment, it is an object of the invention to provide a method of using perfluorocarbon tracers to identify vehicles, comprising of the steps of applying a formulation of perfluorocarbon tracers in a paint or aerosol spray to a vehicle, and detecting the vehicle remotely based on perfluorocarbon emissions.

According to a further embodiment of the invention, a PFT is provided as a part of a food or liquid product, for human ingestion. Preferably, the PFT is provided in a PFT-polyphosphazene matrix, in such form as it will not release until heated or otherwise changed chemically. The PFT can be detected by urinalysis, breath testing, of other body fluid testing. Vapor emissions may be used to detect the location of a tagged individual.

The numerous modifications and variations of the present invention are possible in light of the above teachings. It is therefore understood that within the scope of the appended claims, the invention may be practiced otherwise than as specifically described herein.

What is claimed is:

1. A tracing method, comprising:
   (a) providing a tracer comprising a liquid perfluorinated tracer having at least one of (i) a —$CF_2$—$CF_2$— portion, or (ii) spectral characteristics corresponding to highly electronegative fluorine substituents of an organic composition, encapsulated within at least one permeable wall capsule having a first composition within a polymer matrix having a second composition, the polymer matrix having a controlled matrix permeability for the perfluorinated tracer, wherein the polymer matrix substantially causes a steady state release rate of the perfluorinated tracer into air for an extended period;
   (b) physically blocking a release of the perfluorinated tracer with an electronically controlled barrier substantially impermeable to the perfluorinated tracer;
   (c) altering the electronically controlled barrier to permit contact of the polymer matrix with air, to thereby permit a release of the perfluorinated tracer into the air, wherein prior to changing the electronically controlled barrier, the release of perfluorinated tracer is undetectable and after changing the electronically controlled barrier the release of perfluorinated tracer is detectable.

2. The method according to claim 1, further comprising concurrently releasing a plurality of different perfluorinated tracer compositions, each having a unique detection characteristic.

3. The method according to claim 1, further comprising selectively controlling a rate of perfluorinated tracer release over time.

4. The method according to claim 1, further comprising removeably attaching the tracer to a human.

5. The method according to claim 1, further comprising covertly attaching the tracer to a vehicle.

6. The method according to claim 1, wherein the polymer matrix comprises a polyphosphazene.

7. The method according to claim 1, further comprising remotely detecting release of perfluorinated tracer.

8. The method according to claim 1, wherein the polymer matrix comprises at least perfluorcarbon-functionalized phosphazene units.

9. The method according to claim 1, wherein the first composition comprises a cyclodextrin.

10. The method according to claim 1, further comprising formulating the polymer matrix with a plurality of different monomers, to selectively control a release rate of the perfluorinated tracer, wherein the release rate is selectively controlled over a range of uniform release rates in dependence on a composition and proportion of the plurality of different monomers.

11. The method according to claim 10, wherein the permeable wall of the at least one capsule has a sufficient permeability to saturate the polymer matrix with perfluorinated tracer, whereby so long as the polymer matrix is saturated with perfluorinated tracer, the release rate of the tag is substantially independent of a permeability of the permeable wall of the at least one capsule.

12. The method according to claim 1, wherein the perfluorinated tracer is selected from one or more of the group of compositions consisting of PMCH, PMCP, o-PDCH', m-PDCH', p-PDCH', PTCH, PDCB, PFP, PFH, PFPT, PFO, DFCH, OFCP, PFD, and PFMD.

13. A remote detection method, comprising:
   (a) providing a liquid perfluorinated tracer having at least one of (i) a —$CF_2$—$CF_2$— portion, or (ii) spectral characteristics corresponding to highly electronegative fluorine substituents of an organic composition, the liquid perfluorinated tracer being volatile and contained within at least one permeable capsule embedded in a polymer matrix, an external surface of the polymer matrix being configured to slowly release the perfluorinated tracer, wherein a permeability of a wall of the at least one permeable capsule rate to liquid perfluorinated tracer exceeds a permeability of the polymer matrix, such that the rate of volatilization of the perfluorinated tracer from the external surface remains at a steady state until the liquid perfluorinated tracer is exhausted;

(b) providing an electronically controlled barrier substantially impermeable to the perfluorinated tracer to block release of the perfluorinated tracer; and (c) selectively controlling a release of volatilized perfluorinated tracer into an environment by altering the electronically controlled barrier.

14. The method according to claim 13, further comprising concurrently releasing a plurality of different volatilized perfluorinated tracer compositions, each having a unique detection characteristic, and remotely detecting the perfluorinated tracer by determining a presence of perfluorinated tracer in the atmosphere.

15. The method according to claim 13, wherein at least one capsule comprises a polymer shell having a composition different than the polymer matrix.

16. The method according to claim 13, wherein the polymer matrix comprises a polyphosphazene having at least perfluorocarbon substituents.

17. The method according to claim 13, wherein the perfluorinated tracer is selected from one or more of the group of compositions consisting of PMCH, PMCP, o-PDCH', m-PDCH', p-PDCH', PTCH, PDCB, PFP, PFH, PFPT, PFO, DFCH, OFCP, PFD, and PFMD.

18. A tag for tracing an object, comprising:

(a) a tracer comprising a liquid perfluorinated tracer having at least one of (i) a —$CF_2$—$CF_2$— portion, or (ii) spectral characteristics corresponding to highly electronegative fluorine substituents of an organic composition, encapsulated within at least one permeable wall capsule having a first composition;

(b) a polymer matrix having a second composition surrounding the at least one permeable wall capsule, the polymer matrix having a controlled matrix permeability for the perfluorinated tracer, wherein the polymer matrix substantially causes a steady state release rate of the perfluorinated tracer into air for an extended period; and (c) an electronically controlled barrier impermeable to the perfluorinated tracer configured to physically block a release of the perfluorinated tracer from a surface of the polymer matrix;

wherein the first and second compositions are different, and the tracer, at least one permeable wall capsule, and polymer matrix are configured such that a free surface of the polymer matrix emits perfluorocarbon tracer at a steady state rate over an extended duration while liquid perfluorocarbon tracer remains in the at least one permeable wall capsule, after the physical blockage of release of the tracer by the electronically controlled barrier is removed.

19. The tag according to claim 18, wherein the polymer matrix comprises a polyphosphazine polymer matrix.

20. The method according to claim 18, wherein the perfluorocarbon tracer is selected from one or more of the group of compositions consisting of PMCH, PMCP, o-PDCH', m-PDCH', p-PDCH', PTCH, PDCB, PFP, PFH, PFPT, PFO, DFCH, OFCP, PFD, and PFMD.

* * * * *